US010612092B2

(12) United States Patent
Suthanthiran

(10) Patent No.: US 10,612,092 B2
(45) Date of Patent: Apr. 7, 2020

(54) METHODS OF PREDICTING ACUTE REJECTION OUTCOMES

(71) Applicant: Cornell Research Foundation, Inc., Ithaca, NY (US)

(72) Inventor: Manikkam Suthanthiran, Scarsdale, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 15/375,892

(22) Filed: Dec. 12, 2016

(65) Prior Publication Data

US 2017/0088894 A1 Mar. 30, 2017

Related U.S. Application Data

(63) Continuation of application No. 14/500,424, filed on Sep. 29, 2014, now abandoned, which is a continuation of application No. 11/861,655, filed on Sep. 26, 2007, now abandoned.

(60) Provisional application No. 60/848,040, filed on Sep. 26, 2006.

(51) Int. Cl.
| | |
|---|---|
| *C12Q 1/6876* | (2018.01) |
| *A61K 31/56* | (2006.01) |
| *G01N 33/68* | (2006.01) |
| *C07K 16/28* | (2006.01) |
| *A61K 35/14* | (2015.01) |
| *A61K 39/00* | (2006.01) |

(52) U.S. Cl.
CPC ............ *C12Q 1/6876* (2013.01); *A61K 31/56* (2013.01); *A61K 35/14* (2013.01); *C07K 16/28* (2013.01); *C07K 16/2809* (2013.01); *G01N 33/6872* (2013.01); *G01N 33/6893* (2013.01); *A61K 2039/505* (2013.01); *C12Q 2600/106* (2013.01); *C12Q 2600/158* (2013.01); *C12Q 2600/16* (2013.01); *G01N 2333/4703* (2013.01); *G01N 2800/245* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 4,798,824 A * | 1/1989 | Belzer | ...................... | A01N 1/02 |
| | | | | 435/1.2 |
| 5,571,800 A * | 11/1996 | Morris | .................. | A61K 31/706 |
| | | | | 514/49 |
| 6,187,534 B1 | 2/2001 | Strom et al. | | |
| 8,932,808 B1 * | 1/2015 | Sarwal | ................ | C12Q 1/6883 |
| | | | | 435/287.1 |
| 2003/0104371 A1 | 6/2003 | Strom et al. | | |
| 2005/0118655 A1 * | 6/2005 | Weinstock | ............. | A61K 35/62 |
| | | | | 435/7.22 |
| 2005/0238651 A1 * | 10/2005 | Gurtner | ................ | A61K 31/739 |
| | | | | 424/184.1 |
| 2006/0115899 A1 * | 6/2006 | Buckner | ............ | A61K 39/0008 |
| | | | | 435/372 |
| 2006/0194725 A1 * | 8/2006 | Rasmussen | .......... | A61K 9/0019 |
| | | | | 424/145.1 |

FOREIGN PATENT DOCUMENTS

WO WO 2006012641 A2 2/2006

OTHER PUBLICATIONS

Muthukumar et al., "Messenger RNA for FOXP3 in the Urine of Renal-Allograft Recipients," New England Journal of Medicine, 355:22, pp. 2342-2351, Dec. 1, 2005.*
"Antibody," Wikipedia.com, Mar. 7, 2018.*
"Corticosteroid," Wikipedia.com, Mar. 8, 2018.*
Muthukumar et al., "Messenger RNA for FOXP3 in the Urine of Renal-Allograft Recipients," The New England Journal of Medicine, vol. 353, No. 22, Dec. 1, 2005, pp. 2342-2351.*
Muthukumar et al., "Messenger RNA for FOXP3 in the Urine of Renal-Allograft Recipients," The New England Journal of Medicine, vol. 353, No. 22, Dec. 1, 2005, pp. 2342-2351. (Year: 2005).*
Long et al., "Understanding FOXP3: Progress Towards Achieving Transplantation Tolerance", Transplantation, vol. 84, No. 4, pp. 459-461, Aug. 27, 2007, Lippincott Williams & Wilkins.
Watschinger et al., "Mechanisms of Allo-Recognition, Recognition by In Vivo-Primed T Cells of Specific Major Histocoompatibility Complex Polymorphisms Presented as Peptides by Responder Antigen-Presenting Cells 1,2", Transplantation, vol. 57, pp. 572-576, No. 4, Feb. 1994, Williams & Wilkins.
Rieger et al., "Mucosal FOXP3+ regulatory T cells are numerically deficient in acute and chronic GvHD", Blood, 2006, 107: 1717-1723, American Society of Hematology, Washington, DC.
Cote, et al., "Allorecognition", Transfus Clin Biol 2001;8: 318-23, 2001.
Li, et al., "Biochemistry and therapeutic implications of mechanisms involved in FOXP3 activity in immune suppression", Current Opinion in Immunology 2007, 19:583-588, Elsevier.
Marson et al., "FOXP3 occupancy and regulation of key target genes during T-cell stimulation", Nature, vol. 445, 2007, pp. 931-935, Nature Publishing Group.
Zheng, et al., "Genome-Wide analysis of Foxp3 target genes in developing and mature regulatory T cells", Nature, vol. 445, 2007, pp. 936-940, Nature Publishing Group.

(Continued)

*Primary Examiner* — Bradley L. Sisson
(74) *Attorney, Agent, or Firm* — Hoffmann & Baron, LLP

(57) ABSTRACT

A method for assessing risk of losing a transplanted organ by a patient having an episode of acute rejection of the transplanted organ is described. The method includes obtaining from the patient a cell sample from the transplanted organ or peripheral blood, determining a level of FOXP3 in the cell sample, and correlating the level with the risk of loss of the transplanted organ, wherein, compared to a control level, a significantly greater level of FOXP3 in the cell sample from the transplanted organ or a significantly lower level of FOXP3 in the cell sample from the peripheral blood correlates with a decreased risk of loss of the transplanted organ.

6 Claims, 20 Drawing Sheets

(56) References Cited

OTHER PUBLICATIONS

Game et al., "Pathways of allorecognition: Implications for transplantation tolerance", Transplant Immunology, 10, 2002, pp. 101-108, Elsevier.

Bestard et al., "Presence of FoxP3+ regulatory T cells predicts outcome of subclinical rejection of renal allografts", J Am Soc Nephrol 19: 2020-2026, 2008, The American Society of Nephrology.

Fontenot et al., "A well adapted regulatory contrivance: regulatory T cell development and the forkhead family transcription factor Foxp3", Nature Immunology, vol. 6, No. 4, pp. 331-337, Apr. 2005, Nature Publishing Group.

Dijke et al., "Regulatory T cells after organ transplantation: Where does their action take place?", Human Immunology, 2008, 69, 389-398, Elsevier.

Sakaguchi et al., "Immunologic Self-Tolerance Maintained by Activated T cells expressing IL-2 Receptor α-Chains (CD25), Breakdown of a Single Mechanism of Self-Tolerance Causes Various Autoimmune Diseases", The Journal of Immunology, 1995 155: 1151-1164, The American Association of Immunologists.

Parish et al., "Too dangerous to ignore: self-tolerance and the control of ignorant autoreactive T cells", Immunology and Cell Biology, 2008, 86, pp. 146-152, Australasian Society for Immunology, Inc.

Davies et al, "T Cell regulation in adult transplantation tolerance", The Journal of Immunology, 1996, 157:529-533, The American Association of Immunologists.

Larosa et al., "The Innate Immune System in Allograft Rejection and Tolerance", The Journal of Immunology, 2007, 178: 7503-7509, The American Association of Immunologists, Inc.

Nydegger et al., "Histo-Blood group antigens as allo- and autoantigens", Ann. N.Y. Acad. Sci. 1050: 40-51, 2005, New York Academy of Sciences.

Rosen, Hugo R., "Transplantation Immunology: What the clinician needs to know for immunotherapy", Gastroenterology 2008; 134:1789-1801, The AGA Institute.

Sumpter et al., "Role of autoimmunity in organ allograft rejection: a focus on immunity to type V collagen in the pathogenesis of lung transplant rejection", Am. J Physiol Lung Cell Mol Physiol 286: L1129-L1139, 2004.

Roep et al., "Auto- and alloimmune reactivity to human islet allografts transplanted into Type 1 diabetic patients", Diabetes, vol. 48, Mar. 1999, pp. 484-490.

Rudensky, A., "Foxp3 and dominant tolerance", Phil. Trans. R. Soc. B (2005) 360, 1645-1646, The Royal Society.

Fontenot, et al., "Regulatory T cell lineage specification by the forkhead transcription factor Foxp3", Immunity, vol. 22, 329-341, Mar. 2005, Elsevier Inc.

Li, et al., "Noninvasive diagnosis of renal-allograft rejection by measurement of messenger RNA for perforin and granzyme B in urine", N. Engl J Med, vol. 344, No. 13, Mar. 29, 2001, pp. 947-954, Massachusetts Medical Society.

Strom, Terry B., M.D., "Rejection-More Than the Eye Can See", N. Engl J Med 353:22, pp. 2394-2396, Massachusetts Medical Society.

Dijke, et al., "Intragraft FOXP3 mRNA Expression Reflects Antidonor Immune Reactivity in Cardiac Allograft Patients", Transplantation, vol. 83, No. 11, Jun. 15, 2007, pp. 1477-1484, Lippincott Williams & Wilkins.

Muthukumar et al., "Mesenger RNA for FOXP3 in the Urine of Renal-Allograft Recipients," The New England Journal of Medicine, 353:22, Dec. 1, 2005, pp. 2342-2351.

\* cited by examiner

US 10,612,092 B2

METHODS OF PREDICTING ACUTE REJECTION OUTCOMES

This application is a continuation application of U.S. Ser. No. 14/500,424, filed Sep. 29, 2014, which is a continuation application of U.S. Ser. No. 11/861,655, filed Sep. 26, 2007, which asserts priority to U.S. Provisional Application Ser. No. 60/848,040, filed on Sep. 26, 2006. The aforementioned applications are incorporated herein by reference in their entireties.

The invention described in this application was made with funds from the National Institutes of Health, Grant Numbers RO1 AI51652 and AI60706. The United States government has certain rights in the invention.

BACKGROUND OF THE INVENTION

Acute rejection of an organ, transplanted from one human to another, is an important risk factor for allograft failure. The outcome of acute rejection is, however, difficult to predict.

Currently, observation of histologic features in allograft tissue obtained by core needle biopsy is the best predictor whether an acute rejection will respond to anti-rejection therapy. However, the invasive procedure of allograft biopsy is associated with complications such as bleeding, arteriovenous fistula, and even graft loss. Thus, there is a need for a non-invasive method for determining whether a patient suffering from acute rejection of a transplant organ is at risk of loss of the transplanted organ.

SUMMARY OF THE INVENTION

The above need has been met by the present invention, which provides in one embodiment a method for assessing risk of losing a transplanted organ by a patient having an episode of acute rejection of the transplanted organ, the method comprising obtaining from the patient a cell sample from the transplanted organ or from peripheral blood, determining a level of FOXP3 in the cell sample, and correlating the level with the risk of loss of the transplanted organ, wherein, compared to a control level, a significantly greater level of FOXP3 in the cell sample from the transplanted organ or a significantly lower level of FOXP3 in the cell sample from the peripheral blood correlates with a decreased risk of loss of the transplanted organ, or a level of FOXP3 that is not significantly greater in the cell sample from the transplanted organ or a level of FOXP3 that is not significantly lower in the cell sample from peripheral blood correlates with an increased risk of loss of the transplanted organ.

In another embodiment of the present invention, a method for assessing likelihood of responding to anti-rejection treatment by a patient having an episode of acute rejection of the transplanted organ, the method comprises obtaining from the patient a cell sample from the transplanted organ or from peripheral blood, determining a level of FOXP3 in the cell sample; and correlating the level with the likelihood of responding to anti-rejection treatment wherein, compared to a control level, a significantly greater level of FOXP3 in the cell sample from the transplanted organ or a significantly lower level of FOXP3 in the cell sample from the peripheral blood correlates with an increased likelihood of responding to anti-rejection treatment, or a level of FOXP3 that is not significantly greater in the cell sample from the transplanted organ or a level of FOXP3 that is not significantly lower in the cell sample from peripheral blood correlates with a decreased likelihood of responding to anti-rejection treatment.

In another embodiment of the present invention, a method for assessing the likelihood of reversing an acute rejection of a transplanted organ by a patient having an episode of acute rejection of the transplanted organ, the method comprises obtaining from the patient a cell sample from the transplanted organ or from peripheral blood, determining a level of FOXP3 in the cell sample, correlating the level with the likelihood of reversing acute rejection of the transplanted organ, wherein, compared to a control level, a significantly greater level of FOXP3 in the cell sample from the transplanted organ or a significantly lower level of FOXP3 in the cell sample from the peripheral blood correlates with an increased likelihood of reversing acute rejection of the transplanted organ, or a level of FOXP3 that is not significantly greater in the cell sample from the transplanted organ or a level of FOXP3 that is not significantly lower in the cell sample from peripheral blood correlates with a decreased likelihood of reversing acute rejection of the transplanted organ.

DETAILED DESCRIPTION OF THE INVENTION

Figure 1A:
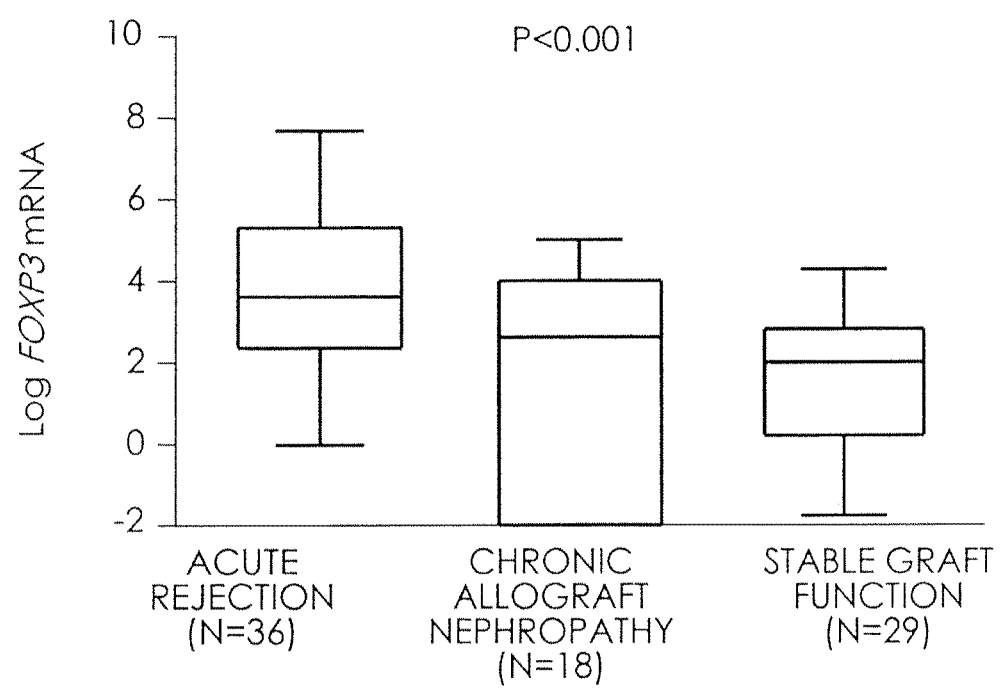
FIG. 1A. Level of FOX3 mRNA in urinary cells. Box plots show the 10th, $25^{th}$, 50th (median), $75^{th}$, and 90th percentile values for log-transformed ratios of mRNA copies to 18S rRNA copies for FOX3 in urine samples obtained from 36 subjects with biopsy-confirmed acute rejection, 18 subjects with biopsy-confirmed chronic allograft nephropathy, and 29 subjects with stable graft function and normal biopsy results. The levels of mRNA for FOX3 were higher in the urinary cells from subjects with acute rejection than in the subjects with chronic allograft nephropathy or normal biopsy results. P values are based on the Kruskal-Wallis test, with the log-transformed mRNA levels treated as the dependent variable. Dunn's multiple-comparison test showed that levels of FOXP3 mRNA in the acute-rejection group were higher than those in both the group with chronic allograft nephropathy ($P<0.05$) and the group with normal biopsy results ($P<0.01$). Log-transformed levels, normalized for 18S rRNA, are shown.

The invention is based on the surprising discovery by the inventor that the level of forkhead box P3 (FOXP3), measured during an episode of acute rejection, in a cell sample from a transplanted organ or from peripheral blood of a patient is useful for assessing the outcome of acute rejection. It has also been discovered by the inventor that, compared to a control level, a significantly greater level of FOXP3 during an episode of acute rejection in the cell sample from the transplanted organ or a significantly lower level of FOXP3 during an episode of acute rejection in the cell sample from the peripheral blood correlates with a decreased risk of loss of the transplanted organ. Similarly, compared to a control level, a level of FOXP3 during an episode of acute rejection that is not significantly greater in the cell sample from the transplanted organ or a level of FOXP3 during an episode of acute rejection that is not significantly lower in the cell sample from peripheral blood correlates with an increased risk of loss of the transplanted organ.

The patient is any human having an episode of acute rejection of a transplanted organ. Any organ suitable for transplantation can be susceptible to an episode of acute rejection. Examples of such organs include kidney, heart, liver, lung, intestines, pancreas, pancreatic islets, etc.

An episode of acute rejection of an organ can be caused by an antibody-mediated or cell-mediated immune response. The cells involved in a cell-mediated immune response include, for example, activated cytotoxic T cells. An episode of acute rejection typically occurs within fourteen days, more typically within ten days, and even more typically within five days after a transplant if the patient is not taking an immunosuppressant drug.

However, most if not all transplant patients are given immunosuppressant drugs. Thus, an episode of acute rejection generally occurs within about one year of a transplanted organ, more generally within about nine months, even more generally within about six months, and most generally within about three months after transplant of an organ. Acute rejection, however, can occur at any time during the life of a transplanted organ. Further, a patient can have more than one episode of acute rejection of a transplanted organ.

In one aspect, the invention provides a method for assessing risk of losing a transplanted organ by a patient suffering from acute rejection of the transplanted organ.

In another aspect, the invention provides a method for assessing likelihood of responding to anti-rejection treatment by a patient suffering from acute rejection of a transplanted organ.

In another aspect, the invention provides a method for assessing the likelihood of reversing an acute rejection of a transplanted organ by a patient suffering from acute rejection of the organ.

Each of the methods of the present invention can be used alone, or in combination with one or more, or all, of the other methods.

The first step in the methods of the present invention comprises obtaining from the patient a cell sample from the transplanted organ or from peripheral blood. Suitable methods for obtaining a cell sample are provided below in the "General Methods" section.

The second step in the methods comprises determining the level of FOXP3 in the cell sample. The determination of the level of FOXP3 in the cell sample can be made by any method known to those skilled in the art. In one embodiment, the level of FOXP3 mRNA or the corresponding level of cDNA is determined. In another embodiment, the level of FOXP3 protein is determined. Suitable methods are provided below in the "General Methods" section.

Method for Accessing Risk of Loss of Transplanted Organ

In this aspect of the present invention, the first and second steps of the method are described above. The next step in the method comprises correlating the level of FOXP3 with the risk of loss of the transplanted organ.

When compared to a control level, a significantly greater level of FOXP3 in the cell sample from the transplanted organ or a significantly lower level of FOXP3 in the cell sample from the peripheral blood correlates with a decreased risk of loss of the transplanted organ. The decreased risk varies in different patients, and the type of organ transplanted. Generally, the decreased risk is at least about 25%, at least about 50%, at least about 75%, or at least about 90%.

When compared to a control level, a level of FOXP3 that is not significantly greater in the cell sample from the transplanted organ or a level of FOXP3 that is not significantly lower in the cell sample from peripheral blood correlates with an increased risk of loss of the transplanted organ. The increased risk varies in different patients, and the organ transplanted. Generally, the increased risk is at least about 25%, at least about 50%, at least about 75%, or at least about 90%.

When the transplanted organ is a kidney, the method for assessing risk of a patient suffering from acute rejection optionally further comprises determining the patient's serum creatinine protein level. The determination of the level of serum creatinine can be made by any method known to those skilled in the art. Suitable methods are provided below in the "General Methods" section below.

The next step in this embodiment comprises correlating the level of serum creatinine in peripheral blood with risk of loss of the transplanted organ. A significantly greater level of serum creatinine in peripheral blood correlates with an increased risk of loss of the transplanted kidney. A level of serum creatinine in peripheral blood that is not significantly greater correlates with a decreased risk of loss of the transplanted kidney.

Generally, the level of serum creatinine in peripheral blood is considered to be significantly greater if the level is at least about 25% greater than the level of creatinine in a control sample.

In this embodiment, a control sample is typically the level of serum creatinine in peripheral blood of a healthy person or a person with a well-functioning (e.g., stable) transplant. For example, the normal level of serum creatinine in a healthy person or a person with a well-functioning transplant is generally about 0.8-1.6 milligrams/deciliter. In either case, the person may be the patient or a person different from the patient.

It is not necessary to determine the level of creatinine in a control sample every time the method is conducted. For example, the serum creatinine level from the patient can be compared to that of one or more previously determined control samples or to a level recognized by the physician or clinician conducting the method, or by a consensus of medical and/or clinical practitioners.

In another embodiment, the method further comprises informing the patient whether the patient is at decreased or increased risk of loss of the transplanted organ. The information that a patient is at risk of loss of a transplanted organ is useful. Such patients can be prescribed and/or administered a treatment to prevent loss of the transplanted organ.

In one embodiment, the treatment comprises administering to the patient an effective amount of a pharmaceutical composition to prevent loss of the transplanted organ. Such pharmaceutical compositions are well known to those skilled in the art, and include, for example a steroid pulse, an antibody, etc.

For example, a steroid pulse therapy can include the administration for three to six days of a high dose corticosteroid (e.g., greater than 100 mg). An example of an antibody therapy includes the administration for seven to fourteen days of the polyclonal antibody antithymocyte globulin (THYMOGLOBIN®) or the monoclonal antibody, muromonab-CD3 (ORTHOCLONE OKT3®).

Another example of a treatment that can be administered is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded.

Method for Assessing Likelihood of Responding to Anti-Rejection Treatment

In this aspect of the present invention, the first and second steps of the method are described above. The next step in the method comprises correlating the level of FOXP3 with the likelihood of the patient in responding to anti-rejection treatment.

When compared to a control level, a significantly greater level of FOXP3 in the cell sample from the transplanted organ or a significantly lower level of FOXP3 in the cell sample from the peripheral blood correlates with an increased likelihood of responding to anti-rejection treatment. The increased likelihood varies in different patients and the type of organ transplanted. Generally, the increased likelihood of responding to anti-rejection treatment means the likelihood is increased by at least about 25%, more preferably by at least about 50%, and even more preferably by at least about 75%. Optimally, the patient responds to anti-rejection therapy such that any risk of complete failure of the transplanted organ is completely eliminated.

When compared to a control level, a level of FOXP3 that is not significantly greater in the cell sample from the transplanted organ or a level of FOXP3 that is not significantly lower in the cell sample from peripheral blood correlates with a decreased likelihood of responding to anti-rejection treatment. The decreased likelihood varies in different patients, and the type of organ transplanted. Generally, the decreased likelihood of responding to anti-rejection treatment means the likelihood is decreased by at least about 25%, by at least about 50%, and even by at least about 75%.

Examples of anti-rejection treatments include those treatment described above for preventing rejection of a transplanted organ.

Method for Assessing Likelihood of Reversing Acute Rejection

In this aspect of the present invention, the first and second steps of the method are described above. The next step in the method comprises correlating the level of FOXP3 with the likelihood of reversing acute rejection of the transplanted organ.

When compared to a control level, a significantly greater level of FOXP3 in the cell sample from the transplanted organ or a significantly lower level of FOXP3 in the cell sample from the peripheral blood correlates with an increased likelihood of reversing acute rejection of the transplanted organ. The increased likelihood varies in different patients and the type of organ transplanted. Generally, the increased likelihood of reversing acute rejection of the transplanted organ means that the likelihood is increased by at least about 25%, more preferably by at least about 50%, and even more preferably by at least about 75%. Optimally, rejection of the transplanted organ is completely eliminated.

When compared to a control level, a level of FOXP3 that is not significantly greater in the cell sample from the transplanted organ or a level of FOXP3 that is not significantly lower in the cell sample from peripheral blood correlates with a decreased likelihood of reversing acute rejection of the transplanted organ. The decreased likelihood varies in different patients and the type of organ transplanted. Generally, the decreased likelihood of reversing acute rejection means the likelihood is decreased by at least about 25%, by at least about 50%, and even by at least about 75%.

General Methods

A cell sample from a transplanted organ or peripheral blood can be obtained from a patient by any method known to those in the art. Examples of such cell samples include transplant tissue biopsy, blood, urine, bile, bronchoalveolar lavage fluid, and pericardial fluid. Suitable methods include, for example, venous puncture of a vein to obtain a blood sample and collection of a urine specimen.

Any method known to those in the art can be employed for determining the level of FOXP3 mRNA. Typically, total RNA, which includes mRNA, is isolated. RNA can be isolated from the sample by any method known to those in the art. For example, commercial kits, such as the TRI Reagent® commercially available from Molecular Research Center, Inc. (Cincinnati, Ohio), can be used to isolate RNA.

The quantification of FOXP3 mRNA from total mRNA from the biological sample can be performed by any method known to those in the art. For example, kinetic, quantitative PCR involves reverse transcribing FOXP3 mRNA by using reverse-transcriptase polymerase chain reaction (RT-PCR) to obtain FOXP3 cDNA. The cDNA can then, for example, be amplified by PCR followed by quantitation using a suitable detection apparatus. See example 1 below for a description of the quantitation of FOXP3 mRNA by kinetic, quantitative PCR.

Generally, the isolated FOXP3 mRNA may be amplified by methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, New York (1995). For example, levels of FOXP3 mRNA can be determined using kinetic, quantitative PCR.

An alternative method for determining the level of FOXP3 mRNA includes the use of molecular beacons and other labeled probes useful in, for example multiplex PCR. In a multiplex PCR assay, the PCR mixture contains primers and probes directed to the FOXP3 PCR product. Typically, a single fluorochrome is used in the assay. The molecular beacon or probe is detected to determine the level of FOXP3 mRNA. Molecular beacons are described, for example, by Tyagi and Kramer (Nature Biotechnology 14, 303-308, 1996) and by Andrus and Nichols in U.S. Patent Application Publication No. 20040053284.

Another method includes, for instance, quantifying cDNA (obtained by reverse transcribing the FOXP3 mRNA) using a fluorescence based real-time detection method, such as the ABI PRISM 7700 or 7900 Sequence Detection System [TaqMan®] commercially available from Applied Biosystems, Foster City, Calif. or similar system as described by Heid et al., (Genome Res. 1996; 6:986-994) and Gibson et al. (Genome Res. 1996; 6:995-1001).

Any method known in the art can be used for determining the protein level of FOXP3 in the cell sample from a transplanted organ or peripheral blood, or serum creatinine levels from peripheral blood.

Suitable methods for determining protein levels include an ELISA and a standard blot. Briefly, these assays are normally based on incubating an antibody specific to the protein with a sample suspected of containing the protein, and detecting the presence of a complex between the antibody and the protein.

Alternatively, commercial kits can be utilized. An example of a commercial kit for determining creatinine level is the QuantiChrom™ Creatinine Assay Kit from BioAssay Systems (Hayward, Calif.).

Generally, the level of FOXP3 in a cell sample is significantly greater if the gene expression of FOXP3 is heightened. For example, a discriminatory level for heightened gene expression (e.g., the baseline magnitude of gene expression) of FOXP3 is defined as the mean±95% confidence interval of a group of values observed in nonrejecting transplants (e.g., control values, i.e., control levels). The group of values as used herein includes, for example, a minimum of at least about 2 values, more preferably a minimum of at least about 10 values, most preferably a minimum of at least about 20 values. The group of values as used herein includes, for example, a maximum of at most about 500 values, more preferably a maximum of at most about 100 values, most preferably a maximum of at most about 50 values.

Heightened gene expression of FOXP3 is considered to be significantly greater if the value is greater than the mean±95% confidence interval of a group of values observed in nonrejecting transplants. Similarly, the level of FOXP3 in the cell sample is considered to be significantly lower if the FOXP3 value is lower than the mean±95% confidence interval of a group of values observed in nonrejecting transplants.

The level of FOXP3 is typically considered not significantly greater if the level of FOXP3 in a cell sample is not greater than the mean±95% confidence interval of a group of values observed in nonrejecting transplants. The level of FOXP3 is normally considered not significantly lower if the level in a cell sample is not lower than the mean±95% confidence interval of a group of values observed in nonrejecting transplants.

Statistical analysis in the above mean±95% confidence interval of a group of values observed in nonrejecting transplants was performed with a $x^2$ test.

In another embodiment, the level of FOXP3 in a cell sample is significantly greater if the log-transformed mean (±SE) ratio of FOXP3 mRNA copies to 18S-rRNA copies is higher relative to a control ratio in nonrejecting organs, as determined by the Kruskal-Wallis test. For example, a significantly greater ratio is typically at least about ±SE 3.0, more typically between ±SE 3.0 and 5.0, and most typically between ±SE 3.8 and 4.7.

Similarly, the level of FOXP3 in a cell sample is significantly lower if the log-transformed mean (±SE) ratio of FOXP3 mRNA copies to 18S-rRNA copies is reduced relative to a control ratio (i.e., control values, control levels) in nonrejecting organs, as determined by the Kruskal-Wallis test. For example, a typical nonrejection organ control ratio is not more than about 2.5, more typically 1.0 to 2.5, and most typically from 1.3 and 2.0.

In yet another embodiment, the control values (control levels) observed in nonrejecting organs, e.g., kidneys, may be defined as the level of FOXP3 of the same patient before the organ transplant; the average level of FOXP3 in patients of similar age, gender, race, graft-donor source, Banff histologic grade, or initial antirejection treatment as the patient; a value for the level of FOXP3 accepted in the art.

In an embodiment of the invention, generally, the level of FOXP3 when compared to a control level may be increased by at least about 10%, at least about 50%, or at least about 100%. The level of FOXP3 when compared to a control level may be decreased by at least about 10%, at least about 50%, or at least about 100% lower than the level of FOXP3 in a control sample.

A control sample is typically the level of FOXP3 from a healthy person or a person with a well-functioning (e.g., stable) transplanted organ. A well-functioning (e.g., stable) transplanted organ may be defined as a transplanted organ without acute rejection, and preferable a transplanted organ that has not developed transplant dysfunction or morphologic evidence of transplant injury in areas of the transplant. For example, a stable functioning kidney transplant may be defined as having a serum creatinine concentration that has not changed by more than approximately 0.2 mg per deciliter during the seven days before and the seven days after collection of the biologic specimen for FOXP3 measurements.

It is not necessary to determine the level of FOXP3 mRNA or FOXP3 protein in a control sample every time the method is conducted. For example, the FOXP3 levels in the cell sample from the transplanted organ or in the cell sample from the peripheral blood can be compared to that of one or more previously determined control samples or to a level recognized by the physician or clinician conducting the method of a consensus of medical and/or clinical practitioners.

EXAMPLES

Example 1. Methods

Study Cohorts.

Urine samples from 83 kidney-transplant recipients were examined. In this group were 36 subjects with graft dysfunction (mean [±SD] creatinine level, 3.6±2.4 mg per deciliter [318.2±212.2 pmol per liter]) and biopsy-confirmed acute rejection (mean age, 41±12 years; 15 men and 21 women; 13 white, 12 black, and 11 with other racial or ethnic backgrounds; with 20 living and 16 deceased donors), 29 subjects with stable allograft function (mean creatinine level, 1.4±0.4 mg per deciliter [123.8±35.4 µmol per liter]) and normal allograft biopsy (mean age, 44±14 years; 15 men and 14 women; 12 white, 4 black, and 13 with other racial or ethnic backgrounds; with 26 living and 3 deceased donors), and 18 subjects with allograft dysfunction (mean creatinine level, 3.1±1.6 mg per deciliter [274.0±141.4 µmol per liter]) and biopsies classified as indicating chronic allograft nephropathy (mean age, 52±12 years; 9 men and 9 women; 9 white, 2 black, and 7 with other racial or ethnic backgrounds; with 5 living and 13 deceased donors).

Seventy-five of the 83 urine specimens were collected before the biopsy procedure, and 8 samples were obtained after the procedure. Formalin-fixed, paraffin-embedded renal-biopsy specimens were stained with hematoxylin and eosin, periodic acid-Schiff, and Masson's trichrome stains and were scored with the use of the Banff 97 classification by a pathologist who was blinded to the results of molecular studies. Immunosuppression consisted of a calcineurin inhibitor-based regimen (cyclosporine or tacrolimus), with the administration of glucocorticoids, antilymphocyte antibodies (muro-monab-CD3 [ORTHOCLONE OKT3®] or antithymocyte globulin), or both for the treatment of acute rejection.

Quantitation of mRNA by Kinetic, Quantitative PCR.

Total RNA was isolated from urine-cell pellets, quantified and reverse transcribed to complementary DNA (cDNA). Oligonucleotide primers and fluorogenic probes were designed and synthesized for the measurement of mRNA levels of FOXP3, CD25, CD3e, perforin, and 18S ribosomal RNA (rRNA).

PCR analysis was performed by a two-step process, a preamplification step followed by measurement of mRNA with an ABI Prism 7700 system. Transcript levels were calculated by a standard curve method, and mRNA copy numbers were normalized with the use of 18S rRNA copy numbers (the number of mRNA copies in 1 pg of RNA divided by the number of 18S rRNA copies in 1 fg of RNA). When no detectable level of a transcript was found, a value equal to half the minimum observed 18S-normalized level was assigned. For an estimation of group means, this method is considered a reasonable substitute for the value of zero or the minimum detected value; moreover, the nonparametric statistical tests of group differences reported below are not affected by the choice of value.

Statistical Analysis.

The levels of mRNA for FOXP3, CD25, CD3ε, perforin, and 18S rRNA deviated from a normal distribution ($P<0.001$), but a log transformation substantially reduced the positive skew. The 18S-normalized level as the dependent variable in a Kruskal-Wallis test to identify any differences among the group with acute rejection, the group with chronic allograft nephropathy, and the group with normal biopsy results and then used Dunn's test for multiple comparisons. The Mann-Whitney test, equivalent to the Kruskal-Wallis test when applied to two groups, was used when mRNA levels were compared between two groups. Spearman's rank-order correlations were used to test for a monotonic association of the 18S-adjusted mRNA transcript levels with serum creatinine levels and time (in days) from kidney transplantation to biopsy. An episode of acute rejection was classified as reversible if the serum creatinine level returned to within 15 percent of the prerejection level within four weeks after the initiation of antirejection treatment. A second end point was the loss of the graft during the first six months after the diagnosis of acute rejection. Receiver-operating-characteristic (ROC) curves were used to analyze mRNA levels in order to determine the cutoff points that yielded the highest combined sensitivity and specificity for predicting the outcome of an episode of acute rejection.

Example 2. Levels of FOXP3 mRNA in Urinary Cells

Figure 1B:
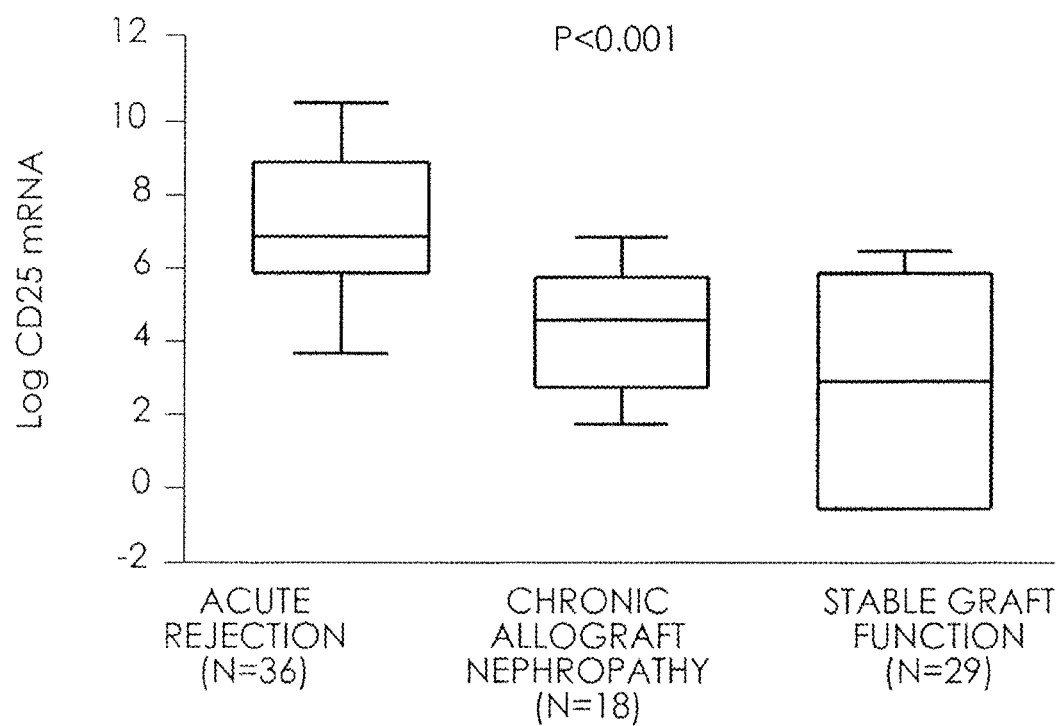
FIG. 1B. Box plots show the 10th, $25^{th}$, 50th (median), $75^{th}$, and 90th percentile values for log-transformed ratios of mRNA copies to 18S rRNA copies for CD25 in urine samples obtained from 36 subjects with biopsy-confirmed acute rejection, 18 subjects with biopsy-confirmed chronic allograft nephropathy, and 29 subjects with stable graft function and normal biopsy results. The levels of mRNA for CD25 were higher in the urinary cells from subjects with acute rejection than in the subjects with chronic allograft nephropathy or normal biopsy results. P values are based on the Kruskal-Wallis test, with the log-transformed mRNA levels treated as the dependent variable. CD25 mRNA levels were higher in the acute-rejection group than in both the group with chronic allograft nephropathy ($P<0.001$) and the group with normal biopsy results ($P<0.001$). Log-transformed levels, normalized for 18S rRNA, are shown.
Figure 1C:
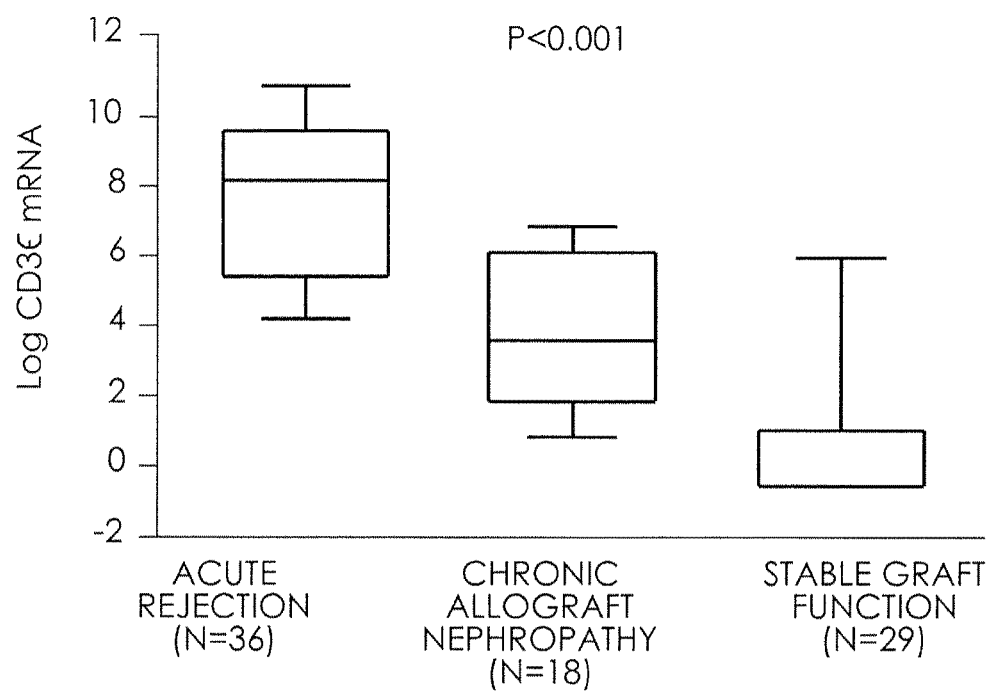
FIG. 1C. Box plots show the 10th, $25^{th}$, 50th (median), $75^{th}$, and 90th percentile values for log-transformed ratios of mRNA copies to 18S rRNA copies for CD3ε in urine samples obtained from 36 subjects with biopsy-confirmed acute rejection, 18 subjects with biopsy-confirmed chronic allograft nephropathy, and 29 subjects with stable graft function and normal biopsy results. The levels of mRNA for CD3ε were higher in the urinary cells from subjects with acute rejection than in the subjects with chronic allograft nephropathy or normal biopsy results. P values are based on the Kruskal-Wallis test, with the log-transformed mRNA levels treated as the dependent variable. CD3ε mRNA levels were higher in the acute-rejection group than in both the group with chronic allograft nephropathy (P<0.01) and the group with normal biopsy results (P<0.001); CD3ε mRNA levels were also higher in the group with chronic allograft nephropathy than in the group with normal biopsy results (P<0.05). Log-transformed levels, normalized for 18S rRNA, are shown.
Figure 1D:
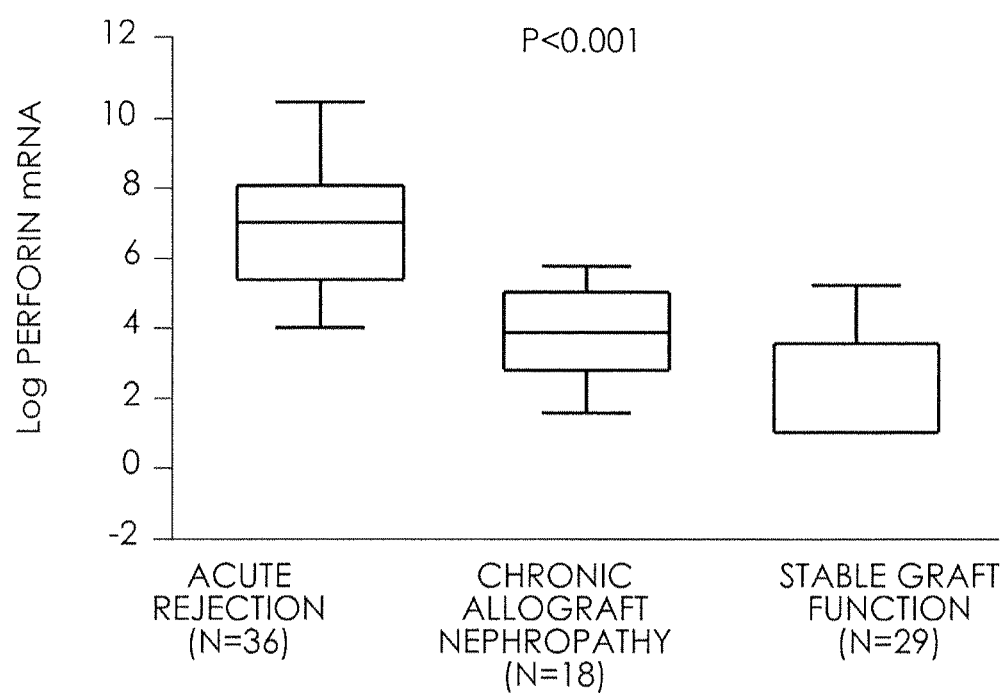
FIG. 1D. Box plots show the 10th, 25th, 50th (median), 75th, and 90th percentile values for log-transformed ratios of mRNA copies to 18S rRNA copies for perforin in urine samples obtained from 36 subjects with biopsy-confirmed acute rejection, 18 subjects with biopsy-confirmed chronic allograft nephropathy, and 29 subjects with stable graft function and normal biopsy results. The levels of mRNA for perforin were higher in the urinary cells from subjects with acute rejection than in the subjects with chronic allograft nephropathy or normal biopsy results. P values are based on the Kruskal-Wallis test, with the log-transformed mRNA levels treated as the dependent variable. Perforin mRNA levels were higher in the acute-rejection group than in both the group with chronic allograft nephropathy (P<0.001) and the group with normal biopsy results (P<0.001). Log-transformed levels, normalized for 18S rRNA, are shown.

The log-transformed mean (±SE) ratio of FOXP3 mRNA copies to 18S-rRNA copies in urinary cells was 3.8±0.5 in the 36 subjects with acute rejection and was higher than the levels in both the 18 subjects with chronic allograft nephropathy (1.3±0.7) and the 29 subjects with normal biopsy results (1.6±0.4, $P<0.001$ by the Kruskal-Wallis test) (FIG. 1A). Among the three groups, the 18S-normalized, log-transformed mRNA levels of CD25 (6.9±0.4, 4.0±0.5, and 2.8±0.6, respectively; $P<0.001$), CD3ε (8.2±0.4, 4.3±0.5, and 1.6±0.5; $P<0.001$), and perforin (7.6±0.4, 4.5±0.4, and 2.8±0.4; P<0.001) were also highest in the acute-rejection cohort (FIGS. 1B, 1C, and 1D).

Example 3. FOXP3 mRNA Levels and Disease Severity

A significant inverse relationship between the levels of FOXP3 mRNA and serum creatinine measured during an episode of acute rejection (Spearman's correlation coefficient [$r_s$]=−0.38, P=0.02). By contrast, serum creatinine levels were not significantly related to mRNA levels of CD25 ($r_s$=−0.01, P=0.93), CD3ε ($r_s$=−0.11, P=0.54), or perforin ($r_s$=−0.23, P=0.18) in the acute-rejection group. Also, the mean (±SE) serum creatinine level in the 16 subjects with acute rejection of Banff grade IA (moderate tubulitis) did not differ significantly from that of the 20 subjects with grade IB (severe tubulitis) or more (3.3±0.6 mg per deciliter [291.7±53.0 µmol per liter] as compared with 3.8±0.6 mg per deciliter [318.2±53.0 µmol per liter], P=0.57).

There was no correlation between the levels of FOXP3 mRNA and serum creatinine that were measured in the group with chronic allograft nephropathy ($r_s$=0.02, P=0.93) or the group with normal biopsy results ($r_s$=−0.08, P=0.67).

Example 4. FOXP3 mRNA Levels and Reversal of Acute Rejection

Figure 2A:
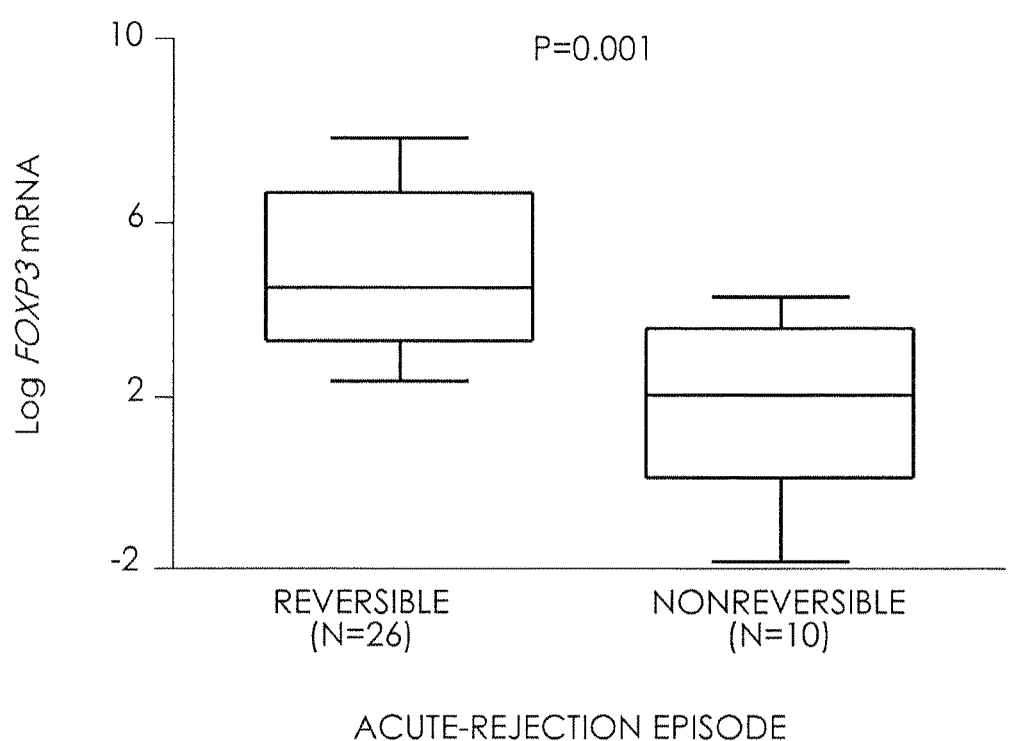
FIG. 2A. Correlation between Levels of FOXP3 mRNA in Urinary Cells and Reversal of an Episode of Acute Rejection. Box plots show the 10th, 25th, 50th (median), 75th, and 90th percentiles for levels of mRNA for FOXP3 in urine samples obtained from 26 subjects with successful reversal of acute rejection (classified as reversible and defined by the return of serum creatinine levels to within 15 percent of prerejection levels within four weeks after the initiation of antirejection treatment) and 10 patients without reversal of acute rejection (nonreversible). The levels of mRNA for FOXP3 were significantly higher in subjects with reversible acute rejection than in subjects with nonreversible acute rejection. Two-tailed P values are based on the Mann-Whitney test. Log-transformed levels, normalized for 18S rRNA, are shown.
Figure 2B:
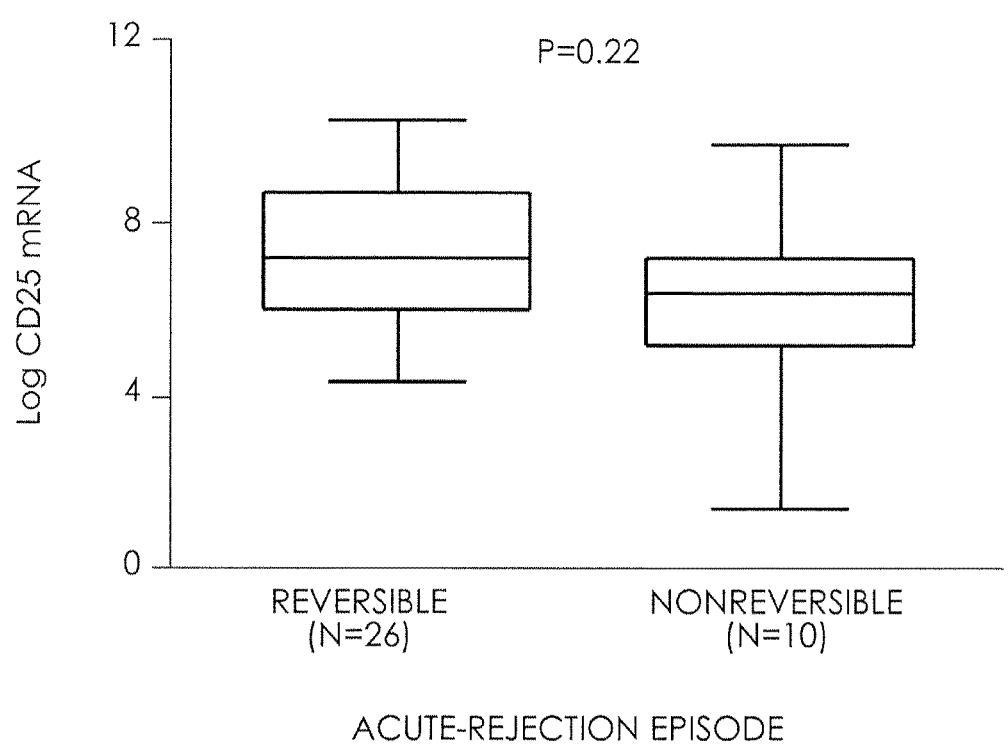
FIG. 2B. Box plots show the 10th, 25th, 50th (median), 75th, and 90th percentiles for levels of mRNA for CD25 in urine samples obtained from 26 subjects with successful reversal of acute rejection (classified as reversible and defined by the return of serum creatinine levels to within 15 percent of prerejection levels within four weeks after the initiation of antirejection treatment) and 10 patients without reversal of acute rejection (nonreversible). The levels of mRNA for CD25 were not significantly higher in subjects with reversible acute rejection than in subjects with nonreversible acute rejection. Two-tailed P values are based on the Mann-Whitney test. Log-transformed levels, normalized for 18S rRNA, are shown.
Figure 2C:
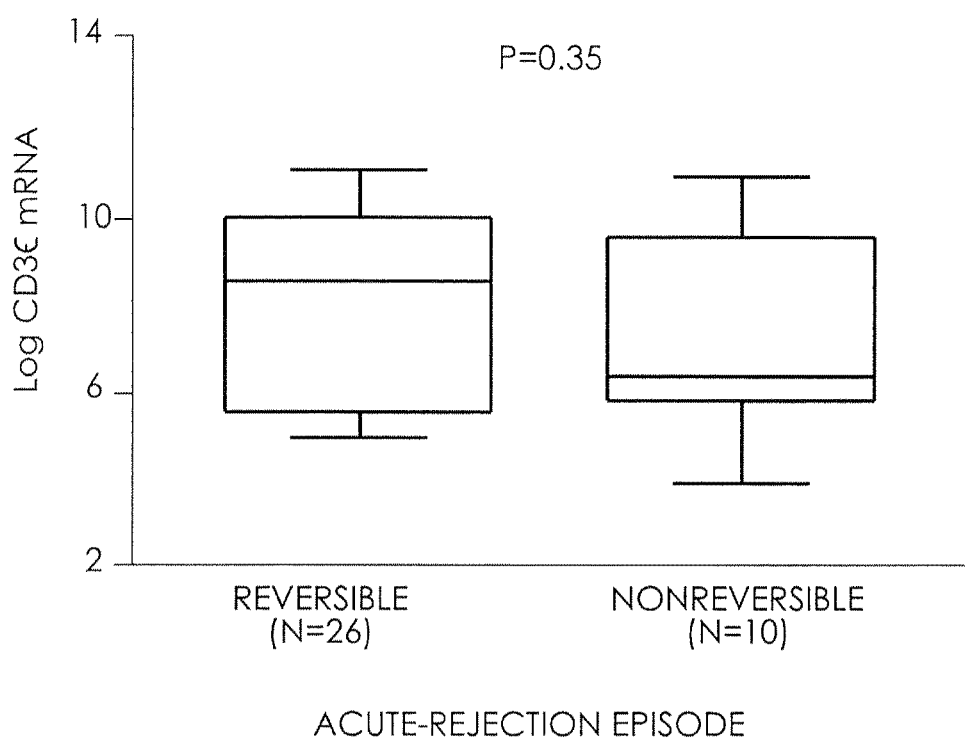
FIG. 2C. Box plots show the 10th, 25th, 50th (median), 75th, and 90th percentiles for levels of mRNA for CD3ε in urine samples obtained from 26 subjects with successful reversal of acute rejection (classified as reversible and defined by the return of serum creatinine levels to within 15 percent of prerejection levels within four weeks after the initiation of antirejection treatment) and 10 patients without reversal of acute rejection (nonreversible). The levels of mRNA for CD3ε were not significantly higher in subjects with reversible acute rejection than in subjects with nonreversible acute rejection. Two-tailed P values are based on the Mann-Whitney test. Log-transformed levels, normalized for 18S rRNA, are shown.
Figure 2D:
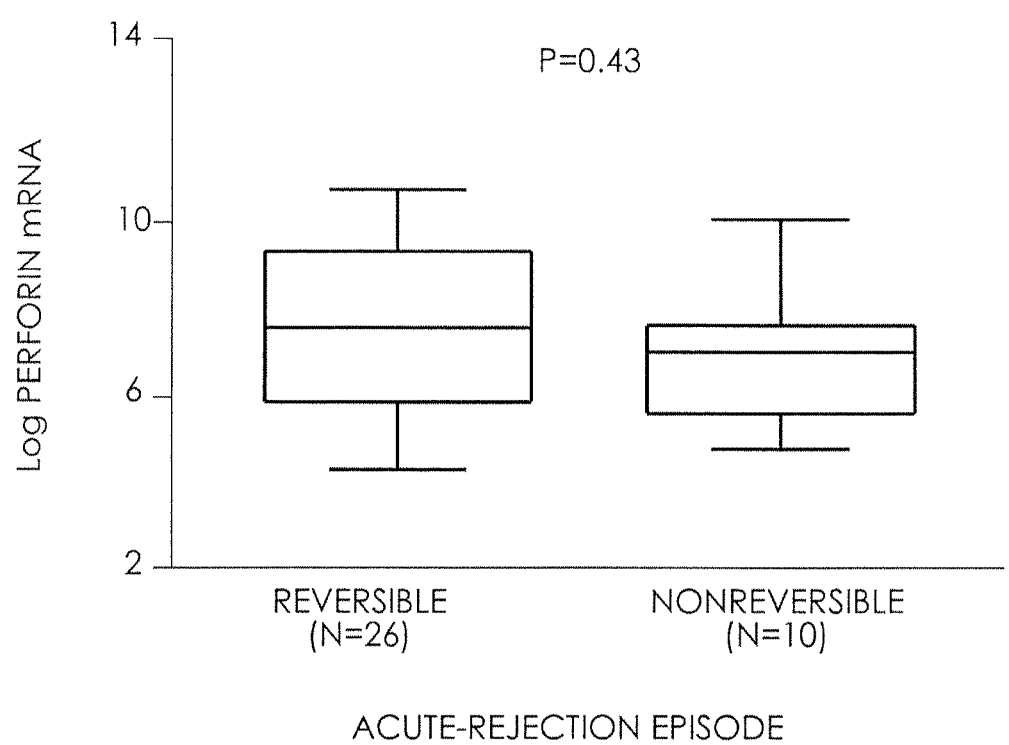
FIG. 2D. Box plots show the 10th, 25th, 50th (median), 75th, and 90th percentiles for levels of mRNA for perforin in urine samples obtained from 26 subjects with successful reversal of acute rejection (classified as reversible and defined by the return of serum creatinine levels to within 15 percent of prerejection levels within four weeks after the initiation of antirejection treatment) and 10 patients without reversal of acute rejection (nonreversible). The levels of mRNA for perforin were not significantly higher in subjects with reversible acute rejection than in subjects with nonreversible acute rejection. Two-tailed P values are based on the Mann-Whitney test. Log-transformed levels, normalized for 18S rRNA, are shown.

Twenty-six of the 36 episodes of acute rejection qualified as successfully reversed; the remaining 10 did not. Levels of FOXP3 mRNA in urinary cells were significantly higher in the group with successful reversal than in the group without reversal (mean [±SE] level, 4.7±0.5 and 1.5±0.7, respectively; P=0.001) (FIG. 2A). In the two groups, the levels of mRNA for CD25 (7.3±0.4 and 6.0±0.9, P=0.22), CD3ε (8.5±0.5 and 7.4±0.8, P=0.35), and perforin (7.8±0.5 and 7.3±0.7, P=0.43) were not informative of outcome (FIGS. 2B, 2C, and 2D).

Figure 3A:
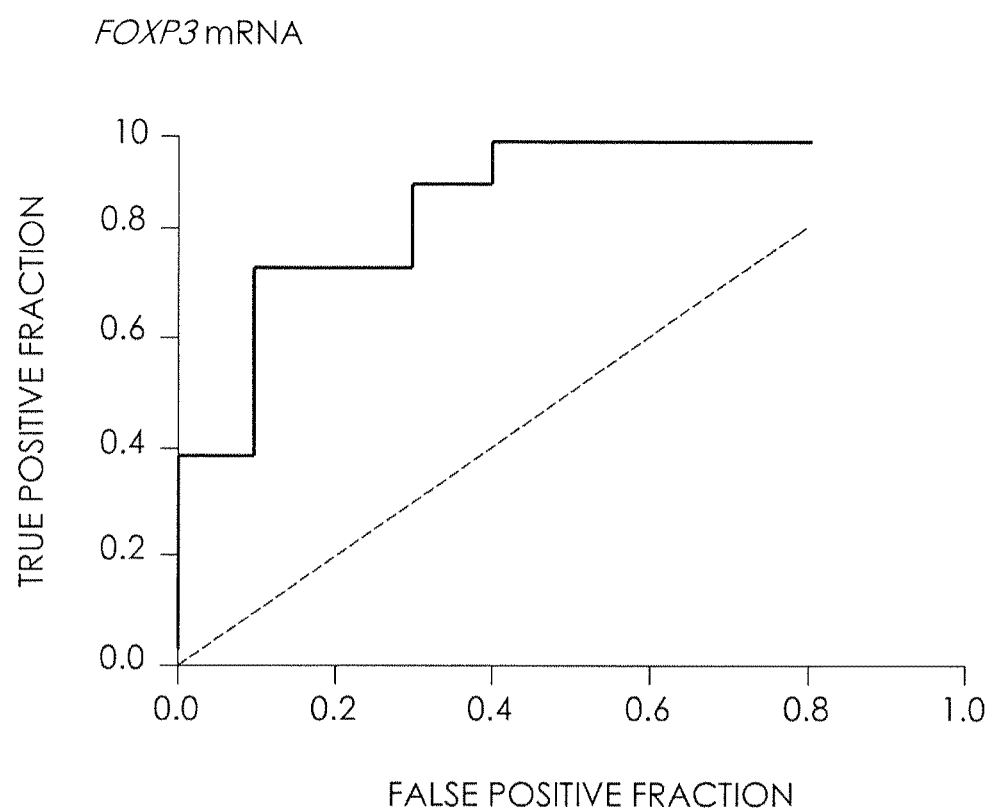
FIG. 3A. Receiver-Operating-Characteristic (ROC) Curves for mRNA Levels. The fraction of true positive results (sensitivity) and false positive results (1-specificity) for levels of mRNA for FOXP3, normalized for 18S rRNA, as predictors of reversal of acute rejection are shown. The calculated area under the curve was 0.85 (95 percent confidence interval, 0.71 to 0.99) for FOXP3 mRNA levels. A P value of 0.5 is no better than that expected by chance (the null hypothesis), and a P value of 1.0 reflects a perfect indicator. FOXP3 predicts successful reversal significantly better than chance (P=0.001).
Figure 3B:
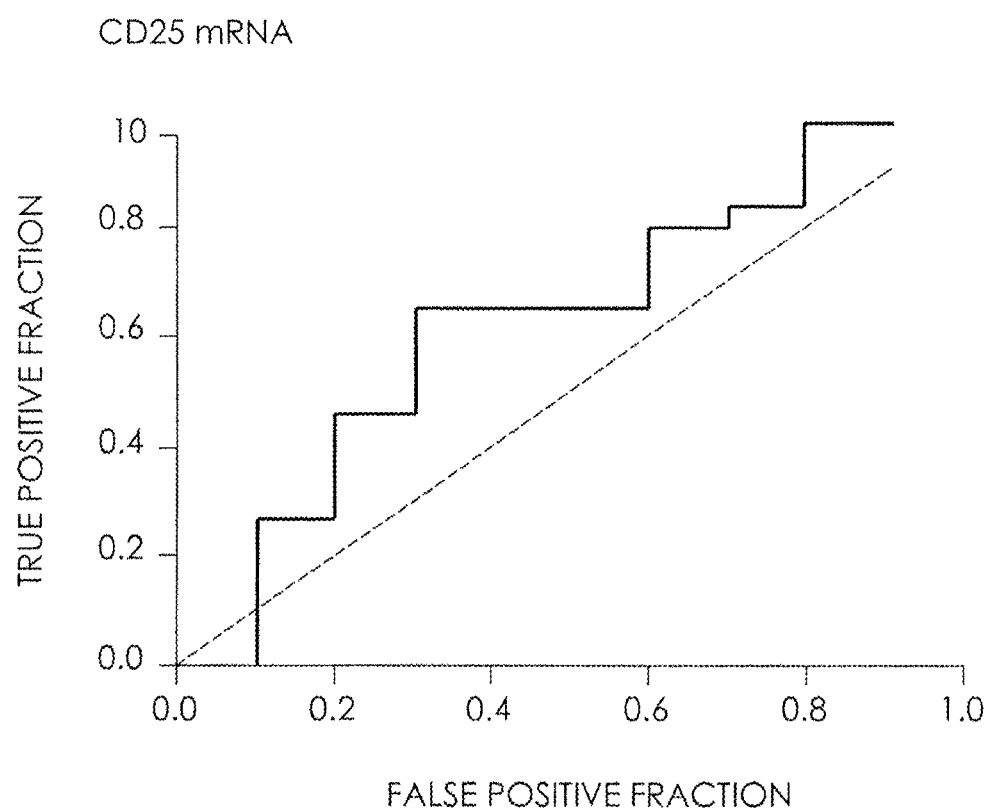
FIG. 3B. Receiver-Operating-Characteristic (ROC) Curves for mRNA Levels. The fraction of true positive results (sensitivity) and false positive results (1-specificity) for levels of mRNA for CD25, normalized for 18S rRNA, as predictors of reversal of acute rejection are shown. The calculated area under the curve was 0.63 (95 percent confidence interval, 0.42 to 0.84) for CD25 mRNA levels. A P value of 0.5 is no better than that expected by chance (the null hypothesis), and a P value of 1.0 reflects a perfect indicator.
Figure 3C:
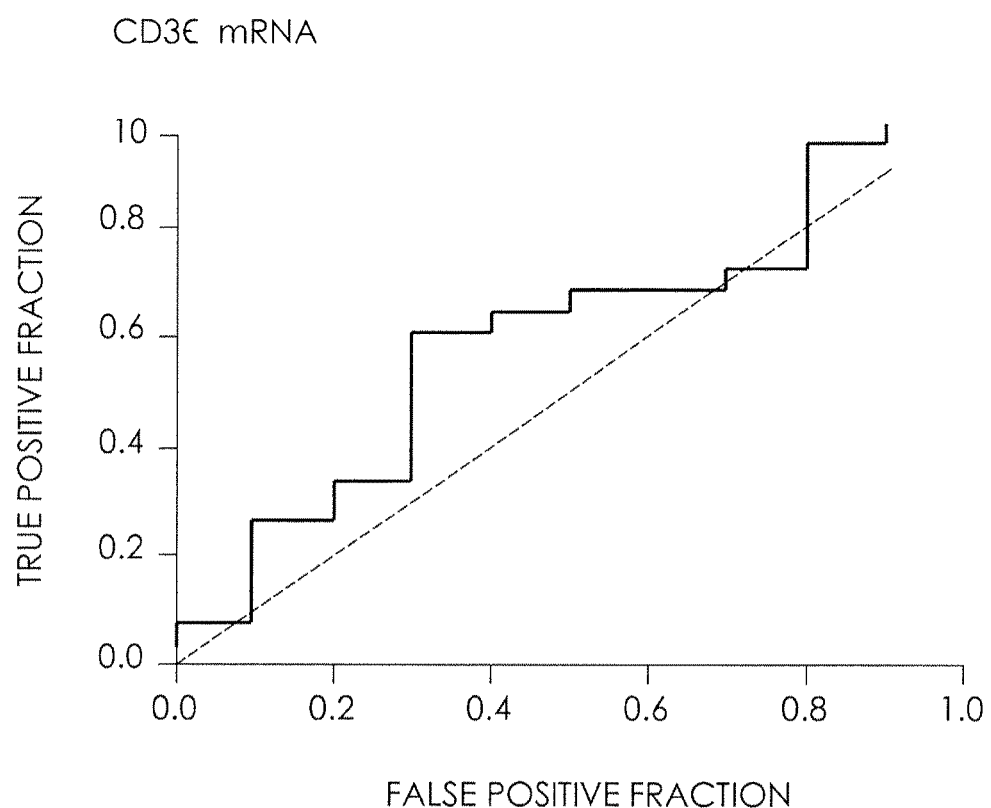
FIG. 3C. Receiver-Operating-Characteristic (ROC) Curves for mRNA Levels. The fraction of true positive results (sensitivity) and false positive results (1-specificity) for levels of mRNA for CD3ε, normalized for 18S rRNA, as predictors of reversal of acute rejection are shown. The calculated area under the curve was 0.60 (95 percent confidence interval, 0.39 to 0.81) for CD3ε mRNA levels. A P value of 0.5 is no better than that expected by chance (the null hypothesis), and a P value of 1.0 reflects a perfect indicator.
Figure 3D:
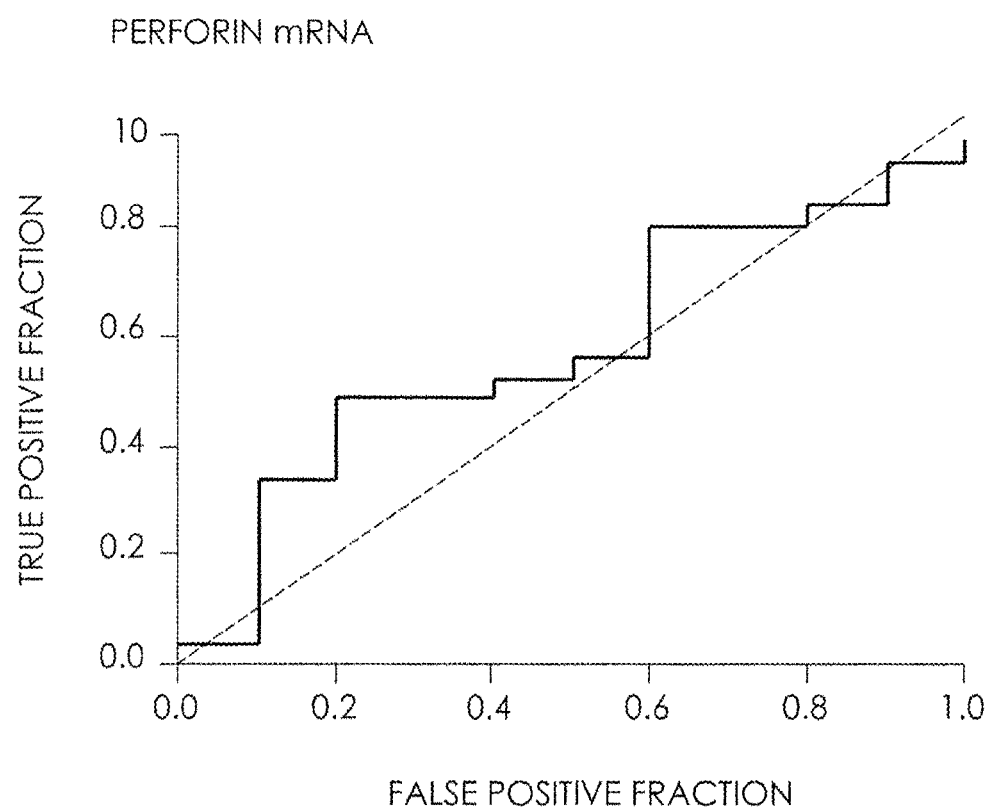
FIG. 3D. Receiver-Operating-Characteristic (ROC) Curves for mRNA Levels. The fraction of true positive results (sensitivity) and false positive results (1-specificity) for levels of mRNA for perforin, normalized for 18S rRNA, as predictors of reversal of acute rejection are shown. The calculated area under the curve was 0.58 (95 percent confidence interval, 0.38 to 0.79) for perforin mRNA levels. A P value of 0.5 is no better than that expected by chance (the null hypothesis), and a P value of 1.0 reflects a perfect indicator.
Figure 4A:
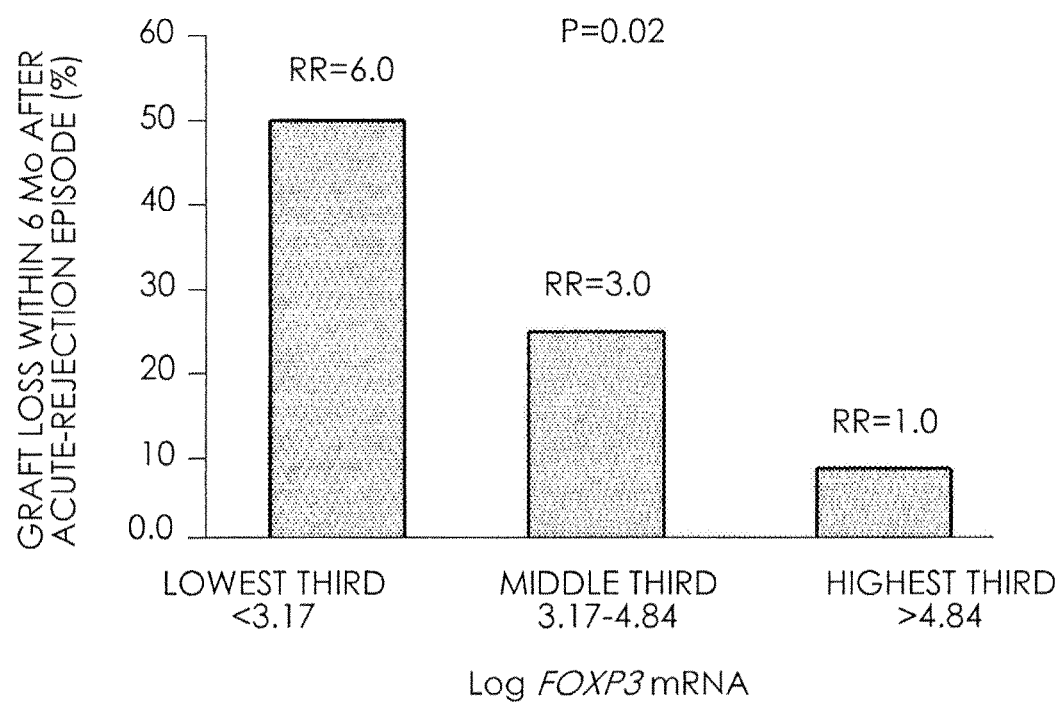
FIG. 4A. Relative Risk (RR) of Graft Failure after an Episode of Acute Rejection. The rates and relative risks of graft failure within six months after an episode of acute rejection for thirds of FOXP3 mRNA levels are shown. The graft-failure rate was 50 percent and the relative risk was 6 for the lowest third of FOXP3 mRNA levels; 25 percent and 3, respectively, for the middle third; and 8 percent for the highest third (P=0.02 by the chi-square test for linear trend).
Figure 4B:
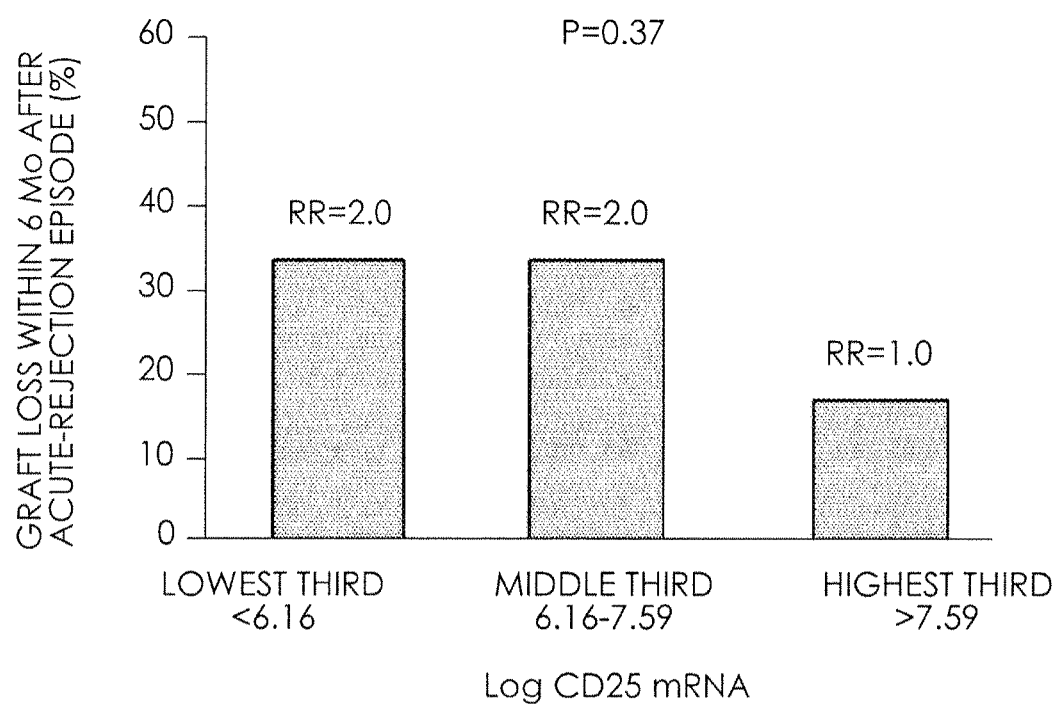
FIG. 4B. Relative Risk (RR) of Graft Failure after an Episode of Acute Rejection. The rates and relative risks of graft failure within six months after an episode of acute rejection for thirds of CD25 mRNA levels are shown. There was no relationship between graft failure after an episode of acute rejection and the thirds of mRNA levels for CD25.
Figure 4C:
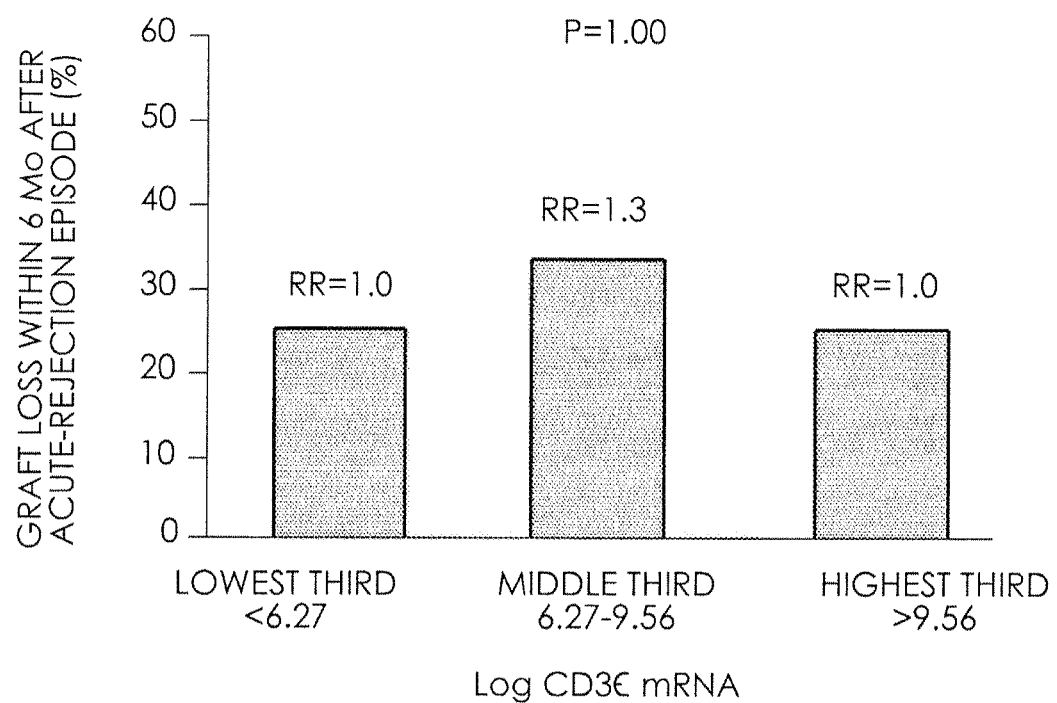
FIG. 4C. Relative Risk (RR) of Graft Failure after an Episode of Acute Rejection. The rates and relative risks of graft failure within six months after an episode of acute rejection for thirds of CD3ε mRNA levels are shown. There was no relationship between graft failure after an episode of acute rejection and the thirds of mRNA levels for CD3ε.
Figure 4D:
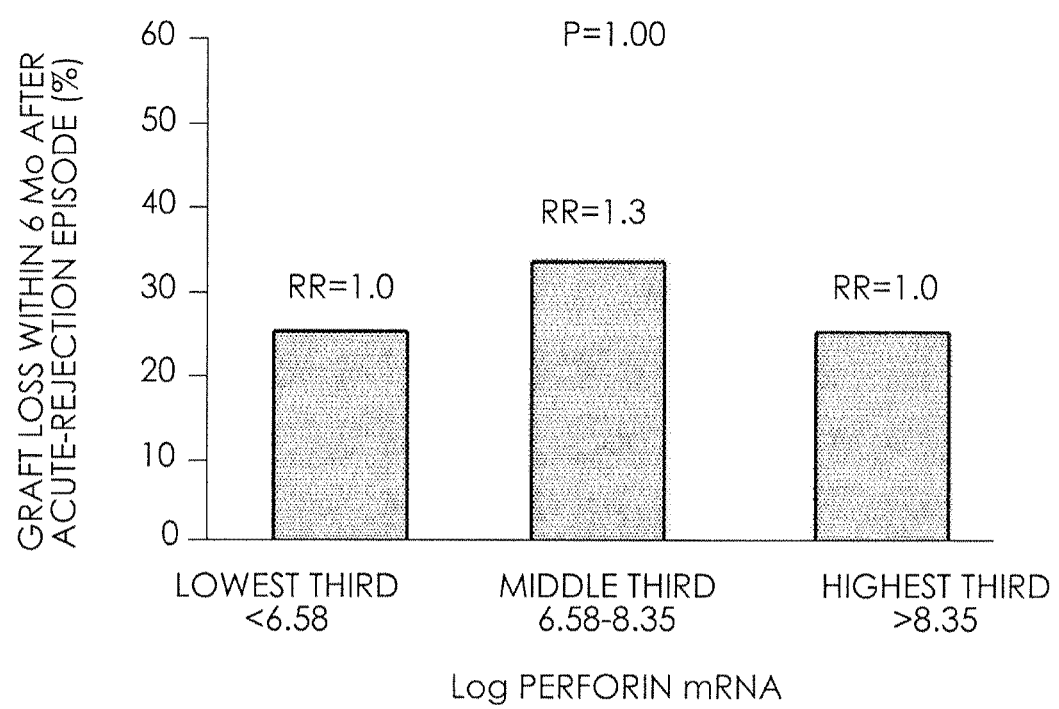
FIG. 4D. Relative Risk (RR) of Graft Failure after an Episode of Acute Rejection. The rates and relative risks of graft failure within six months after an episode of acute rejection for thirds of perforin mRNA levels are shown. There was no relationship between graft failure after an episode of acute rejection and the thirds of mRNA levels for perforin.

The ROC curves (FIG. 3) show the fraction of true positive results (sensitivity) and false positive results (1-specificity) for various cutoff levels of mRNA for FOXP3, CD25, CD3ε, and perforin. The log-transformed threshold that gave the maximal sensitivity and specificity for FOXP3 mRNA was 3.46; using the cutoff value of 3.46 derived from the data, the FOXP3 mRNA level predicted rejection reversal with a sensitivity of 90 percent and a specificity of 73 percent (P=0.001) (FIG. 3A). The levels of mRNA for CD25, CD3ε, and perforin were not predictive of reversal of acute rejection (FIGS. 3B, 3C, and 3D).

Successful reversal of acute rejection, as compared with unsuccessful reversal, was not predicted by the subjects' age (mean [±SD], 41±2.2 years and 40±4.6 years, respectively; P=0.68), sex (10 men and 16 women vs. 5 men and 5 women, P=0.71), race (10 white, 6 black, and 10 with other race or ethnic background vs. 3 white, 6 black, and 1 with other race or ethnic background; P=0.08), graft-donor source (15 living and 11 deceased vs. 5 living and 5 deceased, P=0.68), Banff histologic grade (11 with IA and 15 with >IA vs. 5 with IA and 5 with >IA, P=0.68), or initial antirejection treatment (24 with glucocorticoids and 2 with antilymphocyte antibodies vs. 7 with glucocorticoids and 3 with antilymphocyte antibodies, P=0.12). Among subjects with successful reversal, as compared with those with unsuccessful reversal, serum creatinine levels (median levels, 2.3 mg per deciliter and 6.5 mg per deciliter, respectively; P<0.001) and the time from kidney transplantation to the development of acute rejection (median time, 82 days and 523 days, respectively; P=0.008) were lower. In logistic-regression analyses predicting nonresponse, levels of FOXP3 mRNA in urinary cells remained significant after statistical control for serum creatinine level (P=0.04) and the time from transplantation to rejection (P=0.02).

A linear combination of levels of FOXP3 mRNA and creatinine was a better predictor of rejection reversal (90 percent sensitivity and 96 percent specificity) than FOXP3 mRNA levels alone (90 percent sensitivity and 73 percent specificity) or serum creatinine levels alone (85 percent sensitivity and 90 percent specificity).

Example 5. FOXP3 mRNA Levels and Allograft Failure

Ten of the 36 subjects with acute rejection lost their grafts within six months after the incident episode of acute rejection, and 9 of those 10 subjects did not respond to the initial antirejection therapy. Renal-allograft recipients with a failed allograft within six months after the episode of acute rejection had significantly lower FOXP3 mRNA levels in their urinary cells than the 26 subjects who had a functioning allograft (2.0±0.8 and 4.5±0.5, respectively; P=0.01). In the two groups, the levels of mRNA for CD25 (6.6±0.7 and 7.1±0.5, P=0.33), CD3ε (7.9±0.7 and 8.3±0.5, P=0.76), and perform (7.8±0.6 and 7.6±0.5, P=0.90) did not predict allograft loss.

The rate and relative risk of graft failure within six months after an episode of acute rejection, for thirds of each mRNA measure, are shown in FIG. 4. At the highest third of FOXP3 mRNA levels, the graft failure rate was 8 percent; at the middle third, the graft failure rate was 25 percent and the relative risk was 3; and at the lowest third, the graft failure rate was 50 percent and the relative risk was 6 (P=0.02 by the chi-square test for linear trend) (FIG. 4A). In contrast, the rate of graft failure after an episode of acute rejection did not differ significantly across the thirds of mRNA levels for CD25, CD3ε, and perforin (FIGS. 4B, 4C, and 4D).

Graft failure as compared with graft success was not predicted by the subjects' age (mean [±SD] ages, 39±4.2 years and 42±2.4 years, respectively; P=0.52), sex (4 men and 6 women vs. 11 men and 15 women, P=0.90), race (3 white, 6 black, and 1 with other race or ethnic background vs. 10 white, 6 black, and 10 with other race or ethnic background; P=0.08), graft-donor source (5 living and 5 deceased vs. 15 living and 11 deceased, P=0.68), Banff histologic grade (5 with IA and 5 with >IA vs. 11 with IA and 15 with >IA, P=0.68), or initial antirejection treatment (24 with glucocorticoids and 2 with antilymphocyte antibodies vs. 7 with glucocorticoids and 3 with antilymphocyte antibodies, P=0.12). In subjects with graft failure, as compared with subjects with graft success, serum creatinine levels (median levels, 6.5 mg per deciliter [574.6 µmol per liter] and 2.3 mg per deciliter [203.3 µmol per liter], respectively; P<0.001) and the time from kidney transplantation to the development of acute rejection (median time, 562 days and 82 days; P=0.003) were significantly greater. In a logistic-regression analysis, FOXP3 mRNA levels became nonsignificant after control for serum creatinine levels (P=0.13) or time between transplantation and rejection (P=0.09).

A linear combination of levels of FOXP3 mRNA and creatinine was a better predictor of graft failure (90 percent sensitivity and 92 percent specificity) than were either FOXP3 mRNA levels alone (80 percent sensitivity and 69 percent specificity) or serum creatinine levels alone (85 percent sensitivity and 90 percent specificity).

Example 6. FOXP3 mRNA Levels and Time to Acute Rejection

Figure 5A:
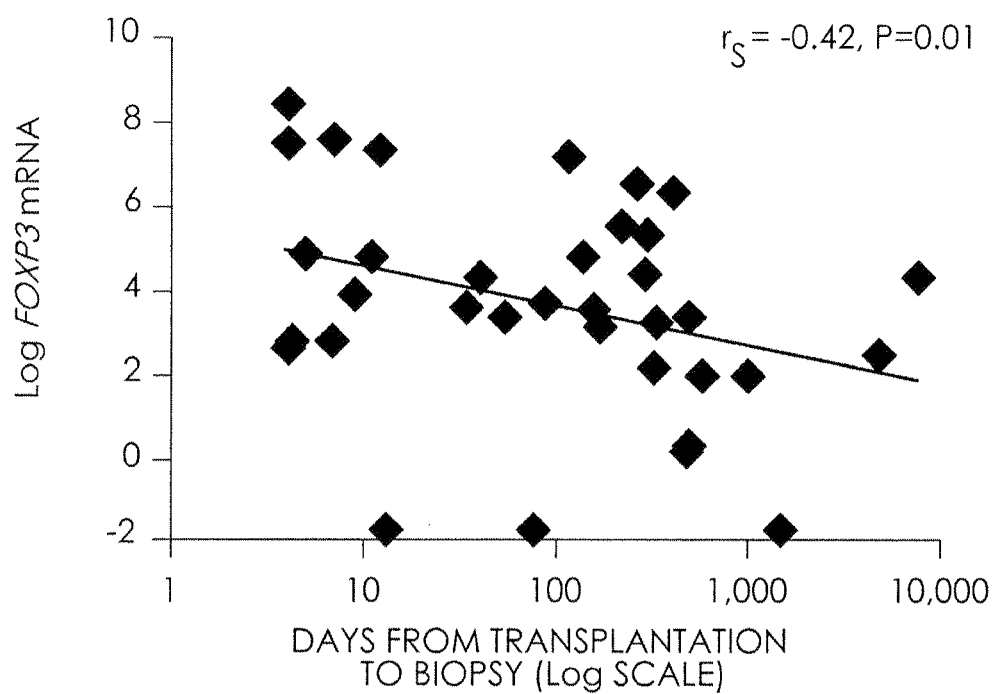
FIG. 5A. Levels of mRNA in Urinary Cells and the Time from Kidney Transplantation to the Development of Acute Rejection. The relationship between levels of mRNA in urine samples and the time from kidney transplantation to the development of biopsy-confirmed acute rejection is shown, along with Spearman's rank-order correlation ($r_s$). A significant inverse relationship between the levels of FOXP3 mRNA in urinary cells and the time from kidney transplantation to the development of acute rejection was found. Log-transformed mRNA levels, normalized for 18S rRNA, are shown. The numbers of days from renal transplantation to the development of acute rejection are shown on a log scale.
Figure 5B:
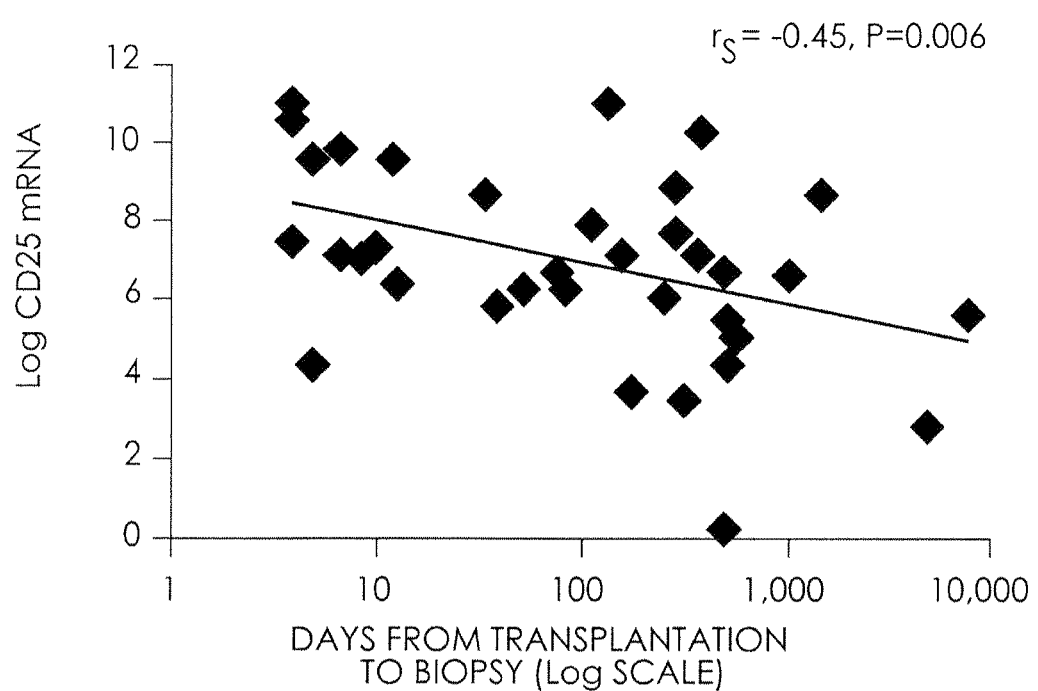
FIG. 5B. Levels of mRNA in Urinary Cells and the Time from Kidney Transplantation to the Development of Acute Rejection. The relationship between levels of mRNA in urine samples and the time from kidney transplantation to the development of biopsy-confirmed acute rejection is shown, along with Spearman's rank-order correlation ($r_s$). A significant inverse relationship between the levels of CD25 mRNA in urinary cells and the time from kidney transplantation to the development of acute rejection was found. Log-transformed mRNA levels, normalized for 18S rRNA, are shown. The numbers of days from renal transplantation to the development of acute rejection are shown on a log scale.
Figure 5C:
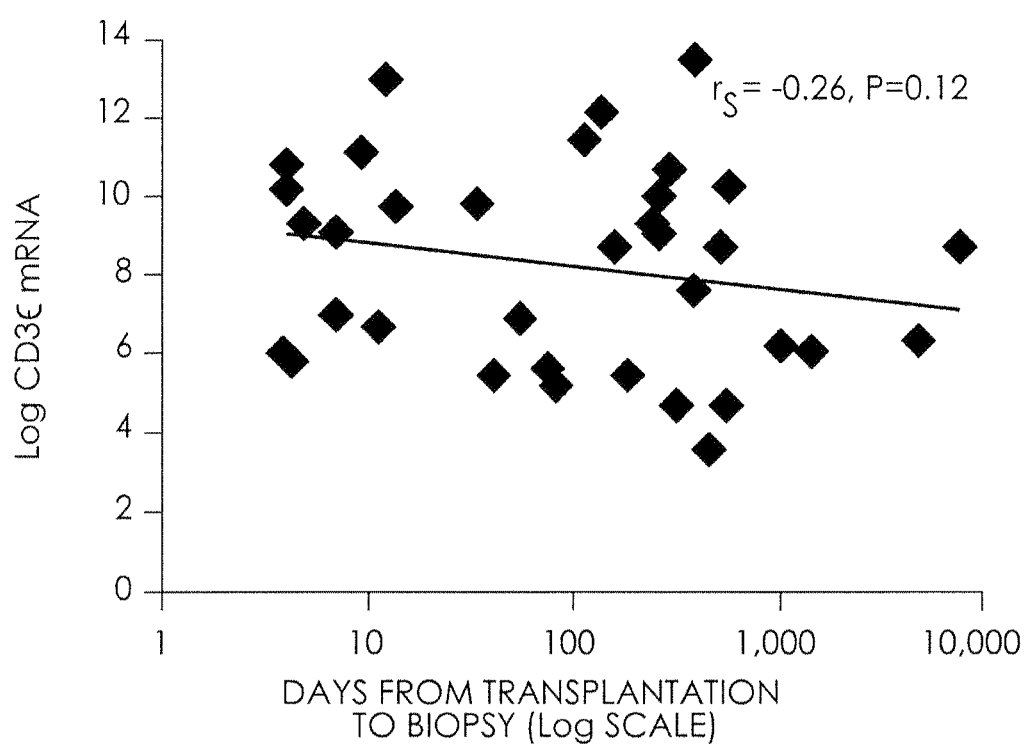
FIG. 5C. Levels of mRNA in Urinary Cells and the Time from Kidney Transplantation to the Development of Acute Rejection. The relationship between levels of mRNA in urine samples and the time from kidney transplantation to the development of biopsy-confirmed acute rejection is shown, along with Spearman's rank-order correlation ($r_s$). There was no significant relationship between levels of CD3ε mRNA in urinary cells and the time from kidney transplantation to the development of acute rejection. Log-transformed mRNA levels, normalized for 18S rRNA, are shown. The numbers of days from renal transplantation to the development of acute rejection are shown on a log scale.
Figure 5D:
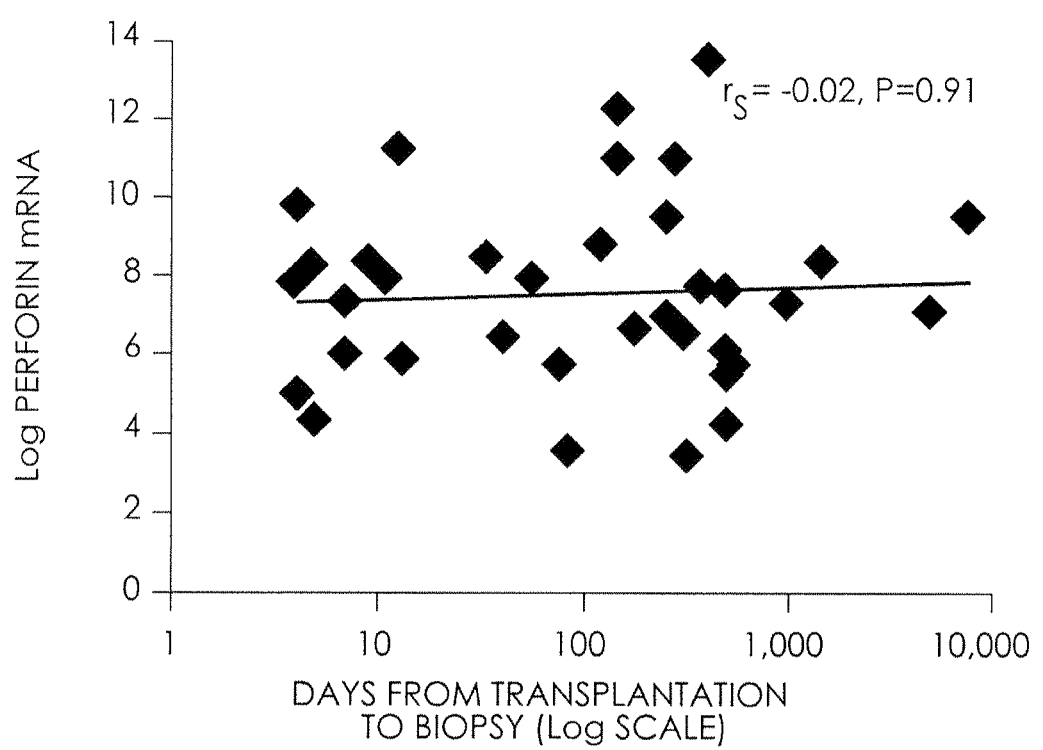
FIG. 5D. Levels of mRNA in Urinary Cells and the Time from Kidney Transplantation to the Development of Acute Rejection. The relationship between levels of mRNA in urine samples and the time from kidney transplantation to the development of biopsy-confirmed acute rejection is shown, along with Spearman's rank-order correlation ($r_s$). There was no significant relationship between levels of perforin mRNA in urinary cells and the time from kidney transplantation to the development of acute rejection. Log-transformed mRNA levels, normalized for 18S rRNA, are shown. The numbers of days from renal transplantation to the development of acute rejection are shown on a log scale.

Late acute rejection (acute rejection occurring at least three months after transplantation) results in an outcome that is inferior to that of early acute rejection. A strong inverse relationship was found between levels of FOXP3 mRNA in urinary cells and the time from kidney transplantation to the development of acute rejection ($r_s$=−0.42, P=0.01) (FIG. 5A). Levels of FOXP3 mRNA in urinary cells were lower in 11 urine specimens from patients with late acute rejection than in 25 specimens from patients with early acute rejection (mean [±SE] level, 2.5±0.6 and 4.7±0.5; P=0.009). CD25 mRNA levels also showed an inverse relation ($r_s$=−0.45, P=0.006) (FIG. 5B), and the levels were lower during late rejection than during early acute rejection (5.8±0.8 and 7.4±0.4, P=0.07). There was no inverse relation between the time from kidney transplantation to the development of acute rejection and the mRNA levels of CD3ε ($r_s$=−0.26, P=0.12) (FIG. 5C) or perforin ($r_s$=−0.02, P=0.91) (FIG. 5D). There was also no correlation between the serum creatinine levels at the time of acute rejection and the time from kidney transplantation to the development of acute rejection ($r_s$=0.23, P=0.17).

Example 7. FOXP3 Levels in Cell Samples from Peripheral Blood are Predictive of Acute Rejection Outcome To determine whether peripheral blood cell FOXP3 mRNA levels are informative of human renal allograft status, peripheral blood, using PAXgene RNA tubes, were collected from 38 renal allograft recipients; 11 subjects with acute rejection and 27 subjects with normal protocol biopsies and stable graft function. Peripheral blood cell mRNA for FOXP3 and mRNA for a constitutively expressed gene 18S ribosomal RNA (18S rRNA) were measured using kinetic quantitative PCR assay. The level of expression, normalized using 18S rRNA copy numbers and log transformed to reduce the positive skew, was correlated with renal allograft status.

Data analyses demonstrated that peripheral blood cell FOXP3 mRNA levels are significantly lower during an episode of acute rejection as compared to levels observed in samples from subjects with normal biopsies and stable graft function (P=0.04, Mann Whitney test). Furthermore, graft outcome following an episode of acute rejection was predicted by peripheral blood cell FOXP3 mRNA levels; there was no graft loss in the lowest tertile, 3 of 4 grafts were lost in the middle tertile, and 2 of 3 grafts failed in the highest tertile.

The invention claimed is:

1. A method for decreasing the risk of losing a transplanted organ by a patient having an episode of acute rejection of the transplanted organ, the method comprising:
   (a) obtaining a cell sample from the patient's peripheral blood or a cell sample from the transplanted organ;
   (b) measuring an amount of gene expression of FOXP3 in the cell sample;
   (c) comparing the amount of gene expression of FOXP3 from the cell sample with a control amount of gene expression of FOXP3 representative of a person without acute rejection of a transplanted organ, and
   (d) administering a pharmaceutical composition or therapy to decrease the risk of losing the transplanted organ, if the amount of gene expression of FOXP3 in the cell sample is at least 10% greater than the control amount,
   wherein the pharmaceutical composition is selected from the group consisting of a calcineurin inhibitor, antithymocyte globulin, muro-monab-CD3, and combinations thereof, and
   wherein the therapy is selected from the group consisting of plasmapheresis and steroid pulse therapy.

2. The method according to claim 1, wherein the amount of gene expression of FOXP3 is an amount of FOXP3 mRNA.

3. The method according to claim 1, wherein the amount of gene expression of FOXP3 is an amount of FOXP3 protein.

4. The method according to claim 1, wherein the transplanted organ is selected from the group consisting of kidney, heart, liver, lung, pancreas, pancreatic islet and intestine.

5. The method according to claim 1, further comprising measuring an amount of serum creatinine in peripheral blood, and correlating the amount with the risk of loss of the transplanted organ, wherein the amount of serum creatinine in peripheral blood that is at least 10% greater than the control amount correlates with an increased risk of loss of the transplanted organ.

6. The method according to claim 1, wherein the calcineurin inhibitor is selected from the group consisting of cyclosporine and tacrolimus.

* * * * *